US011193916B2

(12) United States Patent
MacKenzie et al.

(10) Patent No.: US 11,193,916 B2
(45) Date of Patent: Dec. 7, 2021

(54) CALIBRATION OF A GAS SENSOR

(71) Applicant: SciLogica Corp., Denver, CO (US)

(72) Inventors: Alasdair Allan MacKenzie, Herefordshire (GB); Barry Colin Crane, Oxon (GB); Nicholas Paul Barwell, Warwickshire (GB); Praveen Sagar, Bucks (GB)

(73) Assignee: SCILOGICA CORP., Denver, CO (US)

( * ) Notice: Subject to any disclaimer, the term of this patent is extended or adjusted under 35 U.S.C. 154(b) by 0 days.

(21) Appl. No.: 16/402,040

(22) Filed: May 2, 2019

(65) Prior Publication Data

US 2020/0348275 A1    Nov. 5, 2020

(51) Int. Cl.
*G01N 33/00*      (2006.01)
*G01N 1/22*       (2006.01)
(Continued)

(52) U.S. Cl.
CPC .......... *G01N 33/0006* (2013.01); *G01N 1/22* (2013.01); *G01N 21/63* (2013.01); *G01N 21/64* (2013.01); *G01N 21/6402* (2013.01); *G01N 21/643* (2013.01); *G01N 21/6408* (2013.01); *G01N 21/6486* (2013.01); *G01N 33/00* (2013.01);
(Continued)

(58) Field of Classification Search
None
See application file for complete search history.

(56) References Cited

U.S. PATENT DOCUMENTS 3,612,866 A * 10/1971 Stevens .............. G01N 21/6428
250/483.1
4,476,870 A * 10/1984 Peterson ............ G01N 21/6428
600/312
(Continued)

FOREIGN PATENT DOCUMENTS

WO    WO-2007003674 A2 *  1/2007  ......... G01N 21/6428

OTHER PUBLICATIONS

English Translation (Year: 2007).*
(Continued)

*Primary Examiner* — Herbert K Roberts
*Assistant Examiner* — Fatemeh Esfandiari Nia
(74) *Attorney, Agent, or Firm* — Harness, Dickey & Pierce, P.L.C.

(57) ABSTRACT

There is disclosed a method of calibrating a gas sensor comprising a luminescent compound having a luminescence lifetime that is quenched by a gaseous substance which uses a model of the relationship between the luminescence lifetime and the concentration of the gaseous substance that is modified by a calibration factor representing a proportion of the compound not being exposed to the gaseous substance, the method comprising: measuring values of the luminescence lifetime of the luminescent compound while the gas sensor is exposed to at least two known concentrations of the gaseous substance; and deriving the calibration factor from the measured values of the luminescence lifetime using the model. Also disclosed are a corresponding gas sensor apparatus for measuring the concentration of a gaseous substance in an environment, and method of measuring a concentration of a gaseous substance in an environment using a gas sensor.

31 Claims, 7 Drawing Sheets

(51) Int. Cl.
  *G01N 21/63* (2006.01)
  *G01N 21/64* (2006.01)
  *G01N 33/497* (2006.01)
  *G01N 21/77* (2006.01)
  *G01N 21/78* (2006.01)

(52) U.S. Cl.
  CPC ..... *G01N 33/0004* (2013.01); *G01N 33/0009* (2013.01); *G01N 33/0016* (2013.01); *G01N 33/0018* (2013.01); *G01N 33/497* (2013.01); *G01N 21/6428* (2013.01); *G01N 21/7703* (2013.01); *G01N 21/783* (2013.01); *G01N 2021/6432* (2013.01); *G01N 2021/7786* (2013.01)

(56) References Cited

U.S. PATENT DOCUMENTS

| | | | |
|---|---|---|---|
| 5,012,809 | A | 5/1991 | Schulze |
| 5,030,420 | A * | 7/1991 | Bacon ............... G01N 21/8483 422/82.07 |
| 5,518,694 | A * | 5/1996 | Bentsen ............... G01N 21/274 250/458.1 |
| 6,190,612 | B1 | 2/2001 | Berger et al. |
| 6,531,097 | B1 | 3/2003 | Vojnovic et al. |
| 2002/0164813 | A1 * | 11/2002 | Colvin, Jr. ......... G01N 21/6428 436/95 |
| 2003/0082321 | A1 * | 5/2003 | Kennedy ............ G01N 31/225 428/35.7 |
| 2009/0182210 | A1 | 7/2009 | Taro |
| 2013/0256562 | A1 | 10/2013 | Ward |
| 2013/0280751 | A1 * | 10/2013 | Papkovsky ........ G01N 33/5005 435/29 |
| 2017/0361589 | A1 * | 12/2017 | Vaanhold ........... G01N 21/6408 |
| 2020/0003687 | A1 * | 1/2020 | De Matos Sequeira Berberan E Santos ............... G01F 23/292 |
| 2020/0383618 | A1 * | 12/2020 | Takeuchi ............. A61B 5/1459 |
| 2021/0018423 | A9 * | 1/2021 | Ward ................... G01N 29/222 |

OTHER PUBLICATIONS

Felix Friedl, Investigating the Transfer or Oxygen at the Wavy Air-Water Interface under Wind-Induced Turbulence, (Year: 2013).*

English Translation of WO-2007003674-A2 (Year: 2007).*

Banerjee Swagata et al., High throughput nondestructive assessment of quality and safety of packaged food products using phosphorescent oxygen sensors, Trends in Food Science and Technology, vol. 50, Feb. 1, 2016, pp. 85-102.

Hochreiner H et al., Dual emission probe for luminescence oxygen sensing: a critical comparison between intensity, lifetime and ratiometric measurements, Talanta, Elsevier, Amsterdam, NL, vol. 66, No. 3, Apr. 30, 2005, pp. 611-618.

Perez-Ortiz et al., Determination of the oxygen permeability (Dk) of contact lenses with a fiber-optic luminescent sensor system, Sensors and ActuatorsB: Chemical, Elsevier BV, NL, vol. 126, No. 2, Sep. 19, 2007, pp. 394-399.

B. A. Degraff et al., Luminescence-Based Oxygen Sensors, Reviews in Fluorescence 2005, Springer, US, vol. 2005, pp. 125-151.

Chu, et al., Highly sensitive and linear calibration optical fiber oxygen sensor based on Pt (II) complex embedded in sol-gel matrix, Sensors and Actuators B: Chemical vol. 155 No 1 (2011), p. 53-57.

Escobedo et al., Flexible Passive near Field Communication Tag for Multigas Sensing, Analytical Chemistry vol. 89 (2017), p. 1697-1703.

* cited by examiner

CALIBRATION OF A GAS SENSOR

The present invention relates to methods and apparatuses for measuring the concentration of a gaseous substance in an environment using a gas sensor comprising a luminescent compound.

It is desirable in many areas to be able to determine the concentration of a particular gaseous substance in an environment which may contain a mixture of several different substances, both gaseous and non-gaseous. For example, in clinical settings it is important to be able to accurately determine the concentration of oxygen in a patient's blood in real time to detect and prevent hypoxia. Another example is the monitoring of controlled environments in the food industry, where the presence of oxygen may be undesirable due to the risk of causing spoilage of food. One known type of sensor uses a luminescent compound, for example a fluorescent organic dye, with a luminescence lifetime which depends on the concentration of the target gaseous substance. By exciting the luminescent compound and measuring its luminescence lifetime while it is exposed to the environment, the concentration of the target substance in the environment can be determined. This type of system has the advantage that it can be operated continuously, so does not require taking regular samples, for example of blood or the atmosphere in which food is stored, for analysis or other similarly inconvenient procedures.

The dependence of the luminescence lifetime of many luminescent compounds on the concentration of target gaseous substances is known. Often, the dependence can be modelled using a Stern-Volmer equation, where $\tau_0/\tau$ is linearly dependent on the concentration of the gaseous substance (where $\tau$ is the lifetime observed in the presence of the gaseous substance, and $\tau_0$ is the lifetime in the absence of the substance).

However, in order to manufacture a useful device, the luminescent compound must be incorporated into a sensor. This process can affect the dependence of the luminescence lifetime on the concentration of the target gaseous substance, complicating it relative to the dependence when the luminescent compound is in isolation. For example, where a Stern-Volmer equation would normally be used for the lifetime dependence of the isolated compound, it is observed that $\tau_0/\tau$ is not linearly dependent on the concentration for the sensor-incorporated compound, and a complicated, device-specific calibration procedure is required to fit the observed dependence.

Commonly, several calibration parameters need to be determined due to the complexity of the dependence, making it necessary to calibrate the device in a number of known concentrations of the gaseous substance. This can require complicated, specialist equipment to provide multiple, accurately known gas concentrations. In addition, individual devices may be stored for some time before use, which can lead to changes in the properties of the device that would make a calibration performed at the time of manufacture inaccurate. The combination of these means that end users are required to perform a complicated calibration procedure using expensive, specialised equipment prior to each use of a device. This is inconvenient and time-consuming for the end user.

It is therefore desirable to have a method and apparatus for measuring the concentration of a target gaseous substance using a luminescent compound which does not require a complicated calibration procedure to determine a large number of calibration parameters.

According to a first aspect of the invention, there is provided a method of measuring a concentration of a gaseous substance in an environment using a gas sensor comprising a luminescent compound having a luminescence lifetime that is quenched by the gaseous substance, the method comprising: measuring a value of the luminescence lifetime of the luminescent compound while the gas sensor is exposed to the environment; and deriving a concentration of the gaseous substance from the measured luminescence lifetime using a model of the relationship between the luminescence lifetime and the concentration of the gaseous substance that is modified by a calibration factor representing a proportion of the luminescent compound not being exposed to the gaseous substance.

By using a model representing a proportion of the luminescent compound not being exposed to the gaseous substance, it is possible to account for the effect of incorporating the luminescent compound into the sensor on the luminescence lifetime. This significantly reduces the complexity of the calibration procedure needed to accurately determine the concentration of the gaseous substance from the measured luminescence lifetime. Although the model represents the lifetime as though a proportion of the luminescent compound is not exposed to, or in other words available to interact with, the gaseous substance, this may not be the actual physical mechanism by which the sensor incorporation affects the luminescent compound and its luminescence lifetime. Nonetheless, this model has been found to adequately and accurately account for the behaviour of the luminescent compound.

In an embodiment, the model of the relationship between the luminescence lifetime and the concentration of the gaseous substance is in accordance with a Stern-Volmer equation.

Using a Stern-Volmer relation provides a convenient known starting point for determining the parameters of the model.

In an embodiment, the gas sensor further comprises a temperature sensor configured to measure a temperature of the gas sensor, and the step of deriving a concentration of the gaseous substance takes account of the temperature of the gas sensor measured by the temperature sensor, the model of the relationship between the luminescence lifetime and the concentration of the gaseous substance being dependent on temperature.

It is often the case that the luminescence lifetime is dependent on temperature. By accounting for a temperature dependence when deriving the concentration of the gaseous substance, the method allows for a more accurate determination of the concentration under a wider range of conditions.

In an embodiment, the model of the relationship between the luminescence lifetime and the concentration of the gaseous substance is in accordance with a Stern-Volmer equation, the Stern-Volmer equation including a Stern-Volmer constant that is dependent on temperature, and optionally the Stern-Volmer constant is linearly dependent on temperature.

In an embodiment, the model of the relationship between the luminescence lifetime and the concentration of the gaseous substance is in accordance with a Stern-Volmer equation, the Stern-Volmer equation including a value of the luminescence lifetime in the absence of quenching by the gaseous substance that is dependent on temperature, and optionally the value of the luminescence lifetime in the absence of quenching is linearly dependent on temperature.

These embodiments allow the method to account for temperature dependence of parameters in the model in a straightforward manner. This simplifies analysis of the data while still providing sufficiently accurate readings over temperatures under which the sensor is likely to be used.

In an embodiment, measuring a value of the luminescence lifetime comprises: exciting the luminescent compound using a light source; measuring the intensity of light luminesced by the luminescent compound; and deriving the value of the luminescence lifetime from the measured intensity.

Using controlled illumination of the luminescent compound to measure the luminescence lifetime allows for greater control over the measurement process and improves the accuracy of lifetime measurements used to derive concentrations.

In an embodiment, the environment is inside of a human or animal body, and optionally the gaseous substance comprises oxygen.

In surgical and clinical contexts, it is commonly desirable to monitor the concentration of dissolved gases in the blood of a patient. This allows dangerous conditions to be detected, or for the control of, for example, artificial ventilation. In particular, monitoring of oxygen concentration in a patient's blood is important to prevent hypoxia, which can cause serious and permanent damage to a patient.

In an embodiment, the luminescent compound comprises a platinum complex.

Such complexes are known to have properties suitable for creating a gas sensor.

In an embodiment, the luminescent compound is suspended in a matrix comprising a polymer or a sol-gel, optionally polystyrene.

Suspending the luminescent compound in a matrix provides a convenient way to manufacture the sensor and incorporate the luminescent compound into the sensor. The choice of matrix can affect the response time of the sensor due to solubility of the target gaseous substance in the matrix material. Choosing a suitable matrix is therefore an important consideration in sensor design. Polystyrene has a lower solubility to oxygen than other comparable materials, so is suitable for providing a sensor with a useful response time.

According to a second aspect of the invention, there is provided a method of calibrating a gas sensor comprising a luminescent compound having a luminescence lifetime that is quenched by a gaseous substance which uses a model of the relationship between the luminescence lifetime and the concentration of the gaseous substance that is modified by a calibration factor representing a proportion of the compound not being exposed to the gaseous substance, the method comprising: measuring values of the luminescence lifetime of the luminescent compound while the gas sensor is exposed to at least two known concentrations of the gaseous substance; and deriving the calibration factor from the measured values of the luminescence lifetime using the model.

Using this method allows the system to be calibrated sufficiently accurately while requiring the end user to measure only two data points. This significantly reduces the burden on the end user, saving them time. It also reduces the complexity of equipment that must be available to the end user to provide known gas concentrations to perform the calibration, saving them the expense of acquiring, running and maintaining such equipment.

In an embodiment, one of said known concentrations of the gaseous substance is a concentration of zero.

This choice of a concentration for calibration is particularly convenient, as it allows the lifetime in the absence of the gaseous substance to be determined directly, rather than calculated from two measurements. The sensor may be packaged in an environment free of the target gaseous substance when manufactured, so that the end user can perform this calibration step without any specialised equipment by making a measurement before unpacking the sensor.

In an embodiment, said gaseous substance is present in air and one of said known concentrations of the gaseous substance is the concentration in air.

This is a convenient choice of a calibration point, because it eliminates the need for the end user to possess special equipment to create a known concentration for calibration purposes.

According to a third aspect of the invention, there is provided a gas sensor apparatus for measuring the concentration of a gaseous substance in an environment, the gas sensor apparatus comprising: a gas sensor comprising a luminescent compound having a luminescence lifetime that is quenched by the gaseous substance, and a detector configured to detect light emitted by the luminescent compound; and an analysis system configured to derive a luminescence lifetime of the compound from the signal output by the detector, and to derive a concentration of the gaseous substance from the measured luminescence lifetime using a model of the relationship between the luminescence lifetime and the concentration of the gaseous substance that is modified by a calibration factor representing a proportion of the luminescent compound not being exposed to the gaseous substance.

In an embodiment of the third aspect, the gas sensor further comprises a light source configured to excite the luminescent compound.

Including an illumination source in the gas sensor allows for greater control over the measurement process by controlling the light delivered to the luminescent compound. This improves the accuracy of lifetime measurements used to derive concentrations.

In an embodiment of the third aspect the signal output by the detector represents the intensity of light luminesced by the luminescent compound.

Using changes in luminescence intensity is a well-understood way to measure the luminescence lifetime, allowing the system to make use of known techniques, simplifying the design and manufacture of the sensor.

In an embodiment of the third aspect, the gas sensor comprises an optical fibre, the luminescent compound is arranged at an end of the optical fibre, and the optical fibre is arranged to guide light from the luminescent compound to the detector.

Optical fibres use total internal reflection to prevent light being lost from the fibre. This means light can be efficiently carried to and from the luminescent compound, improving the signal and providing for higher-quality and more reliable measurements. They can also be made small and flexible, so are particularly suitable for sensors that must be inserted into the body of a patient.

In an embodiment of the third aspect the apparatus further comprises a reflector extending around the luminescent compound and configured to reflect light luminesced by the luminescent compound into the optical fibre. Optionally the reflector is permeable to the gaseous substance.

Using a reflector increases the proportion of light emitted by the luminescent compound which can be collected by the optical fibre and subsequently detected. This improves the signal received by the detector, which will in turn improve the accuracy and reliability of the measurements made by the gas sensor apparatus. If the reflector is made permeable to the gaseous substance, it can enclose the luminescent compound completely without affecting its ability to sense the gaseous substance in the environment. This further improves the proportion of light emitted by the luminescent compound which can be collected and transmitted to the detector.

Embodiments of the present invention will now be described by way of non-limitative example with reference to the accompanying drawings, in which.

Figure 1:
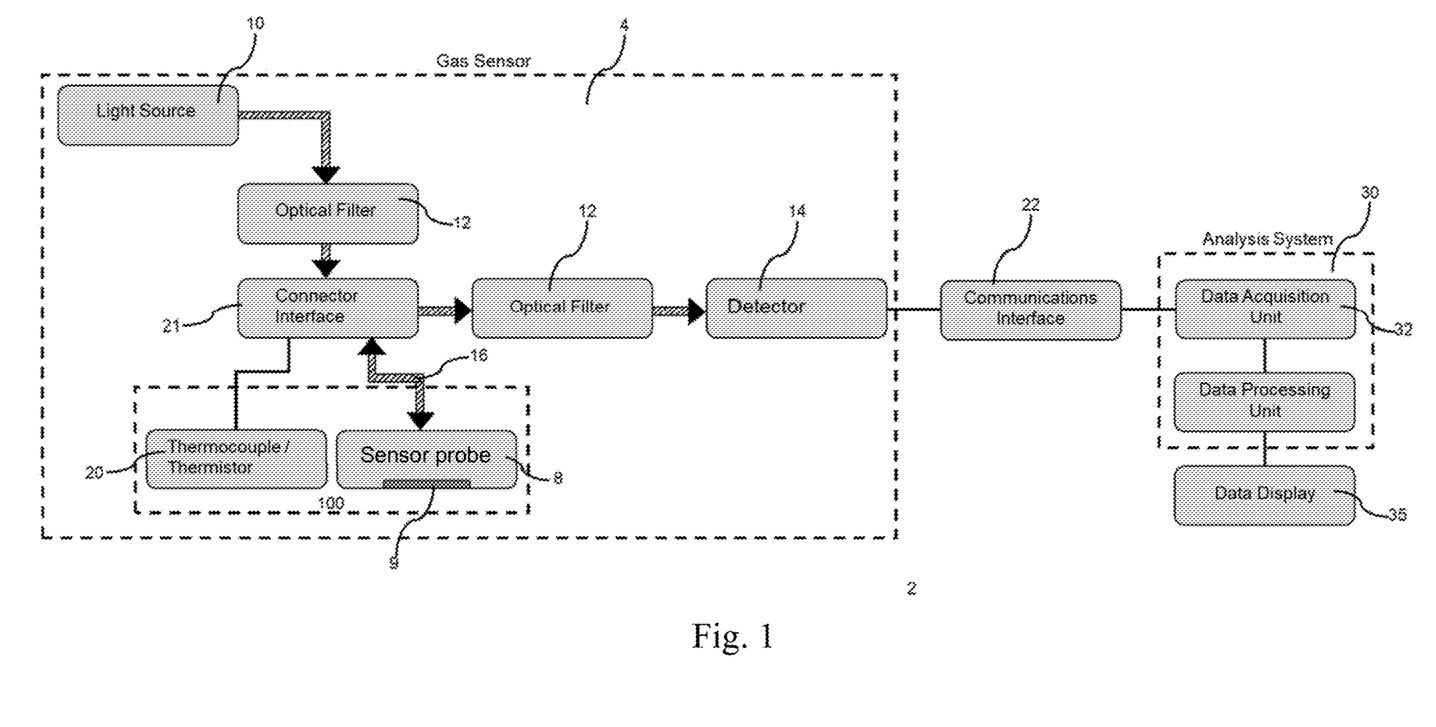
FIG. 1 shows a schematic view of a gas sensor apparatus.

FIG. 1 shows the system architecture for an embodiment of such a gas sensor apparatus 2 for measuring the concentration of a gaseous substance in an environment 100. The gaseous substance may be present in the environment 100 in a gaseous form, or alternatively it may be dissolved or suspended in another substance in the environment 100, for example a liquid such as interstitial fluid or blood. An example of such a gas sensor apparatus 2 may be an oxygen sensor for sensing oxygen concentrations.

The gas sensor apparatus 2 comprises a gas sensor 4 comprising a luminescent compound having a luminescence lifetime that is quenched by the gaseous substance. This means that the luminescence lifetime of the luminescent compound is shorter at higher concentrations of the gaseous substance. An example of such a luminescent compound, in the case that the gas sensor apparatus 2 is an oxygen sensor for sensing oxygen concentrations, is a platinum complex.

The gas sensor 2 comprises a sensor probe 8 in which the luminescent compound is provided. The sensor probe 8 may be the component of the gas sensor 4 which is directly exposed to the environment 100 in which the gaseous substance is to be measured.

The gas sensor 4 comprises a matrix 9 (shown schematically in FIG. 1) and the luminescent compound is suspended in, dissolved in, or molecularly bonded to, the matrix 9. The matrix 9 is a part of the sensor probe 8. The matrix 9 may comprise any material which is stable in the environment 100 and capable of supporting the luminescent compound.

The gas sensor 4 further comprises a light source 10 configured to excite the luminescent compound. The light source 10 may be any light source capable of emitting light at the wavelengths and intensities required to excite the luminescent compound. Typically, this is dependent on the nature of the luminescent compound. For example, the light source 10 may comprise a laser diode. Preferably, the light emitted by the light source 10 is filtered by an optical filter 12 before being transmitted to the luminescent compound. The optical filter 12 is used to ensure only light at the wavelengths necessary to excite the luminescent compound is transmitted to the luminescent compound. This reduces background noise and unexpected sources of excitation, providing greater control and consistency of excitation of the luminescent compound. The light source 10 may be a continuous light source with oscillating intensity, or a pulsed light source.

The gas sensor 4 further comprises a detector 14 configured to detect light emitted by the luminescent compound. The detector 14 may be any device capable of producing a signal in response to receiving light at the wavelengths emitted by the luminescent compound. For example, the detector 14 may comprise a charge-coupled device, an active-pixel sensor, a photodiode, or photoresistor.

The signal output by the detector 14 may represent the intensity of light luminesced by the luminescent compound. This provides a convenient way to measure the lifetime of the luminescent compound, as described further below.

The gas sensor 4 comprises an optical fibre 16, wherein the matrix 9 in which the luminescent compound is suspended is arranged at an end of the optical fibre 16, and the optical fibre 16 is arranged to guide light emitted by the luminescent compound to the detector 14. Optical fibres use total internal reflection to prevent light being lost from the fibre. This means light can be efficiently carried to and from the luminescent compound, improving the signal and providing for higher-quality and more reliable measurements. They can also be made small and flexible, so are particularly suitable for sensors that must be inserted into the body of a patient. Arranging the luminescent compound at one end of the optical fibre 16 is a convenient way to ensure light is transmitted directly to and from the luminescent compound. For example, the optical fibre 16 may comprise a PM_MA fibre optic. The optical fibre may comprise a polyimide sheath 18 attached at the end of the fibre 16 at which the luminescent compound is arranged. Any other suitable light guide, for example an optical waveguide, may be used in place of the optical fibre when appropriate.

Optionally, a reflector 19 is provided extending around the luminescent compound and configured to reflect light luminesced by the luminescent compound into the optical fibre 16. The reflector 19 increases the proportion of light emitted by the luminescent compound which can be collected by the optical fibre 16 and subsequently detected, improving the signal received by the detector 14. The reflector 19 comprises a layer deposited over the luminescent compound, for example the reflector 19 may comprise a layer of polysulfone. The reflector 19 may be chosen to be permeable to the gaseous substance to be detected. This means that the reflector 19 can completely cover the luminescent compound, maximally increasing the light transmitted to the optical fibre 16, while not affecting the sensitivity of the luminescent compound to the gaseous substance.

The gas sensor 4 comprises a temperature sensor 20 configured to measure a temperature of the gas sensor 4. The temperature sensor 20 may be incorporated into the sensor probe 8, or may be separate to it. The temperature sensor 20 may comprise a thermocouple or thermistor.

Some or all of the gas sensor 4 may be disposable. This is convenient in clinical contexts, where the gas sensing apparatus 2 is used to sense gas concentrations inside the body of a patient. In such cases, the part of the gas sensing apparatus 2 which is inserted into the body must be sterile and cannot be reused between patients. For example, in the case where the gas sensor 4 comprises a sensor probe 8, only the sensor probe 8 comprising the luminescent compound may be disposable and not the detector 14 or light source 10. In such a case, the gas sensor 4 further comprises a connector interface 21 configured to connect the sensor probe 8 to the light source 10 and the detector 14.

The gas sensing apparatus 2 further comprises an analysis system 30 configured to derive a luminescence lifetime of the luminescent compound from the signal output by the detector 14. The analysis system 30 is connected to the gas sensor 4 via a communications interface 22. The communications interface 22 may comprise a wired connection, for example a serial or Ethernet connection, or another interface type specifically designed for the gas sensing apparatus. Alternatively a wireless connection, such as Bluetooth® or Wi-Fi may be used. The communications interface 22 transmits the signals output by the detector 14 to the analysis system 30. It also allows signals from the analysis system 30 to be transmitted to the gas sensor 4, for example to control the light source 10.

In general, there are two methods of measuring luminescence lifetime. The first is to measure the luminescent intensity decay curve, and the second is to measure the phase difference.

In the first method, a pulse of light is supplied by the light source 10 to the luminescent compound to excite the luminescent compound. The luminescent compound then emits light with an intensity which decays over time after the pulse of light ends. By measuring the change in intensity during the time after the end of the pulse, the luminescence lifetime can be determined.

In the second method, the light source 10 applies light continuously, but with oscillating intensity. The light emitted by the luminescent compound will also oscillate in intensity. The luminescence lifetime can be determined using the phase difference between the oscillations in the light used to excite the luminescent compound, and the oscillations in the light emitted by the luminescent compound. Either method is suitable for use in the present gas sensing apparatus 2, but the chosen method may affect the specific requirements on the detector 14 and light source 10.

Therefore, in an embodiment where the light source 10 is a continuous light source with oscillating intensity, the analysis system 30 will be configured to derive a luminescence lifetime of the luminescent compound from the signal output by the detector 14 using the phase difference between the oscillations in the light used to excite the luminescent compound, and the oscillations in the light emitted by the luminescent compound.

In an embodiment where the light source 10 is a pulsed light source, the analysis system 30 will be configured to derive a luminescence lifetime of the luminescent compound from the signal output by the detector 14 by measuring the change in intensity during the time after the end of a pulse.

The analysis system 30 is configured to derive a concentration of the gaseous substance from the measured luminescence lifetime using a model of the relationship between the luminescence lifetime and the concentration of the gaseous substance. This model is discussed in more detail below.

In an embodiment where the gas sensor 4 comprises a temperature sensor 20, the analysis system is configured to derive a concentration of the gaseous substance taking account of the temperature of the gas sensor 4 measured by the temperature sensor 20.

The gas sensing apparatus 2 comprises a display device 35 connected to the analysis system 30. The display device 35 displays the concentration of gaseous substance determined by the analysis system 30 in a convenient format for the user. It may also display other information derived from the gas sensor apparatus 2, for example the temperature of the gas sensor 4, or an estimated error or uncertainty in the determined concentration.

The present gas sensing apparatus 2 is particularly suited to use in clinical contexts. The gas sensor 4 or sensor probe 8 can be made very small for insertion into a patient's body. The gas sensing apparatus 2 may be used to measure the concentration of gases dissolved in a patient's blood. Of particular interest are gases important to metabolism, such as oxygen or carbon dioxide. For example, the gas sensing apparatus 2 may be used as part of a control system for a ventilator. In such a case, the concentration of the gaseous substance measured by the gas sensing apparatus 2 is used to control the ventilator to maintain an appropriate range of oxygen concentration in the patient's blood, for example to prevent hypoxia. Another example would be the measurement of oxygen to control oxygenation parameters during a cardiac bypass procedure. Alternatively, the gas sensing apparatus 2 may be used to detect a concentration of anaesthetic in a patient's blood to help with maintaining an appropriate level of anaesthesia during a surgical procedure.

Figure 2:
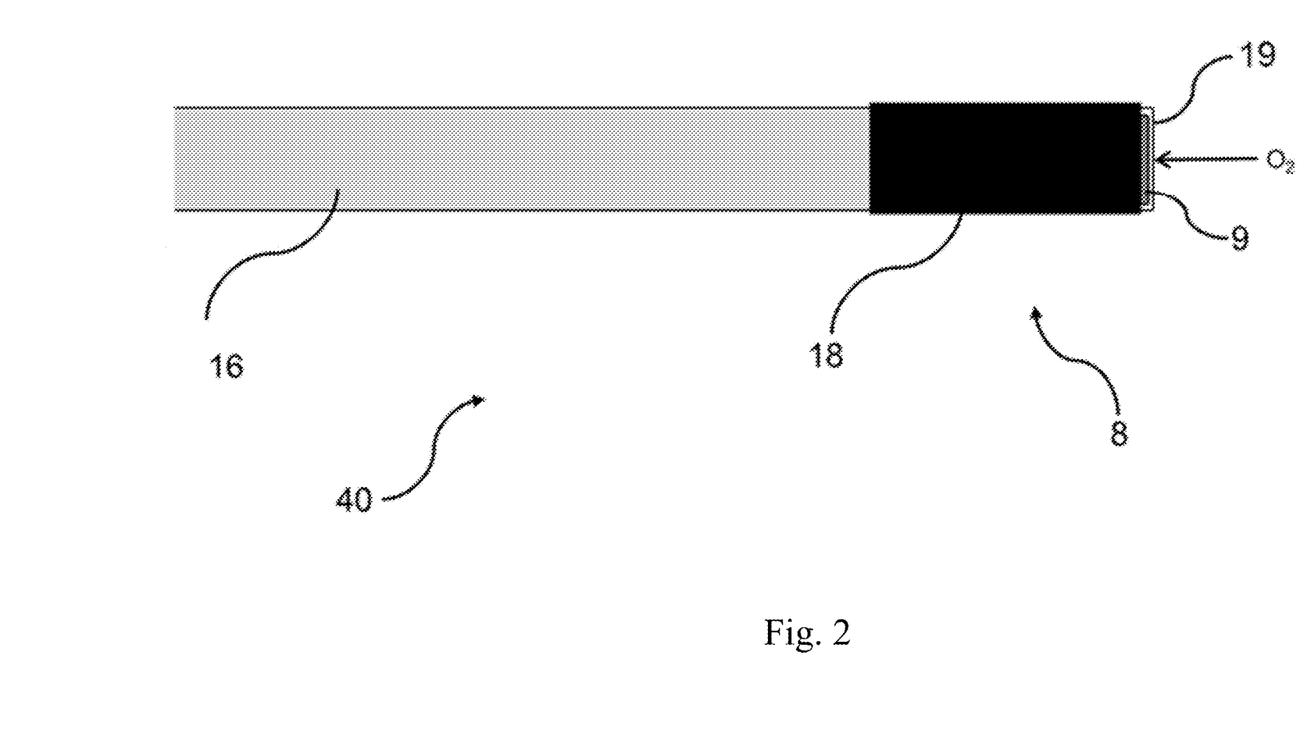
FIG. 2 shows an example of an intravascular gas sensor.
Figure 3:
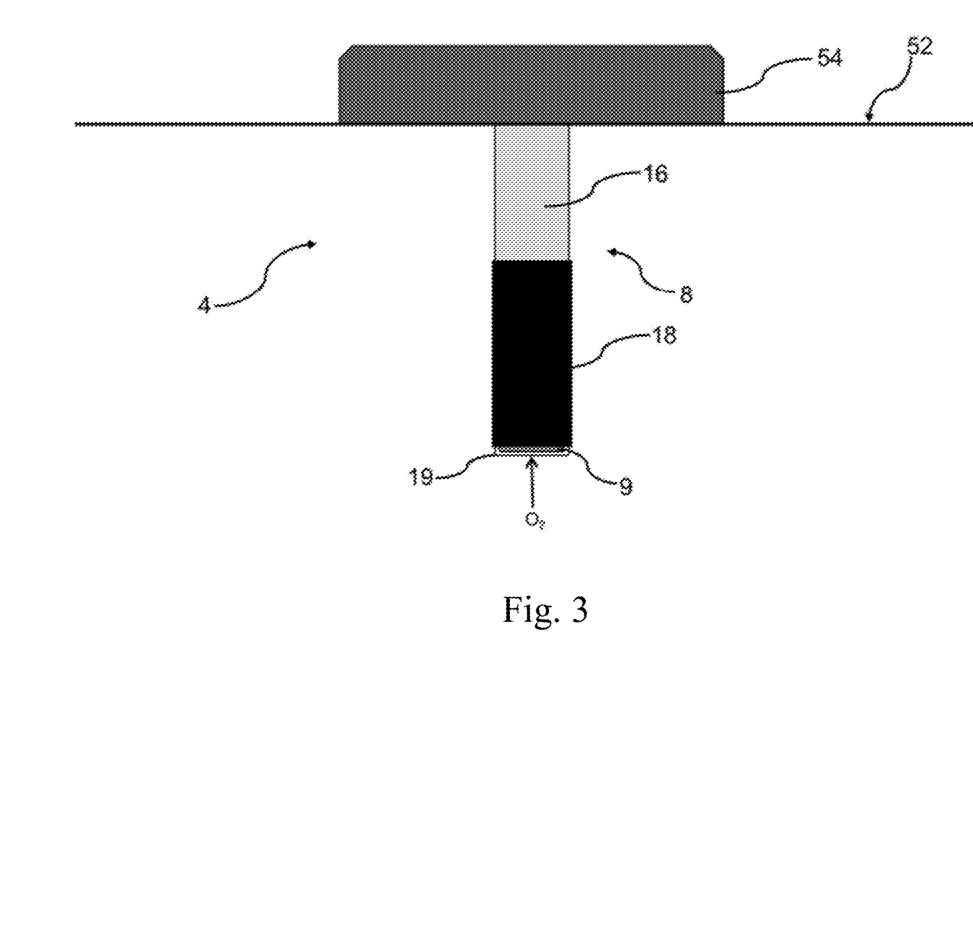
FIG. 3 shows an example of an interstitial gas sensor.
Figure 4:
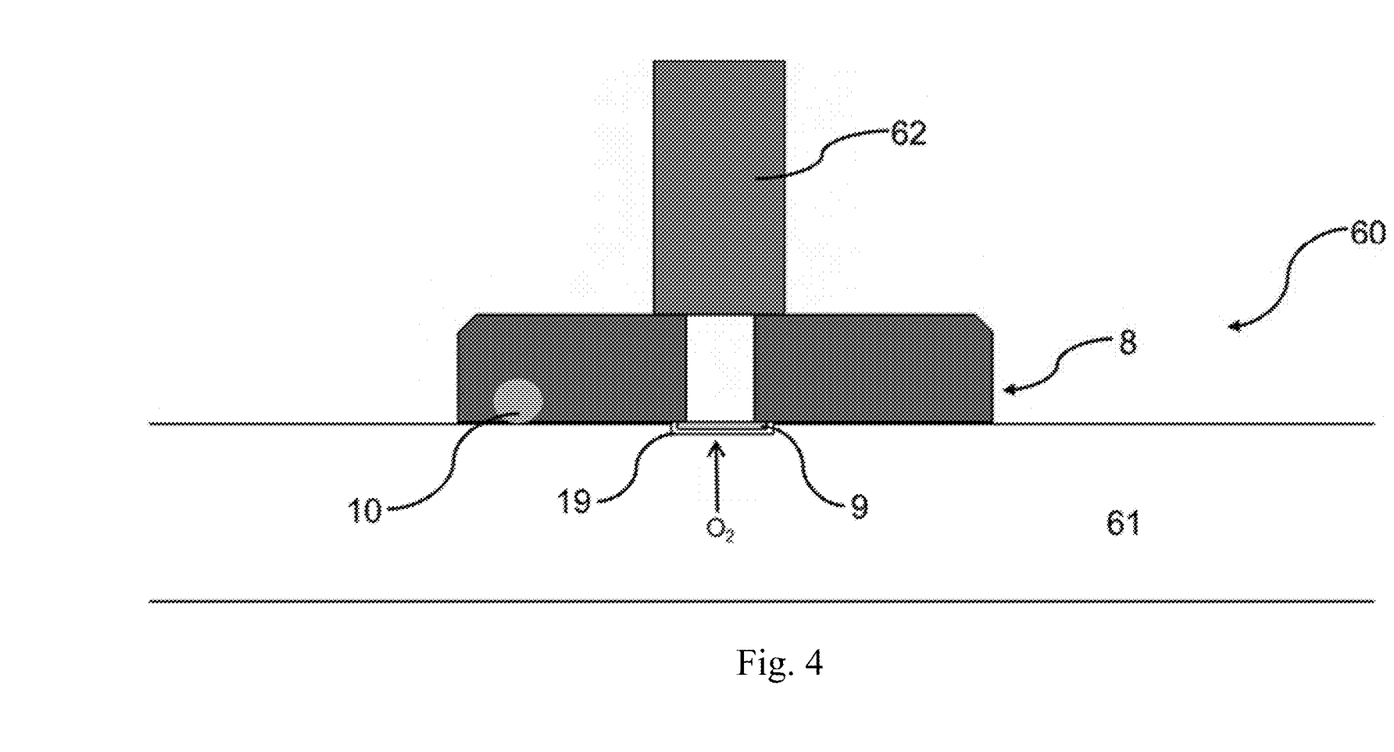
FIG. 4 shows an example of a bypass gas sensor.

FIGS. 2 to 4 show some specific example embodiments of the gas sensor 4 for use in clinical contexts and in the case that the gas sensor 4 comprises a sensor probe 8.

FIG. 2 shows a diagram of an embodiment in which the gas sensor 4 is an intravascular sensor 40. The luminescent compound is located on the tip of an optical fibre 16 that is inserted into the patient via a catheter. The sensor probe 8 contains the fibre optic 16 along with a temperature sensor 20 comprising a thermocouple or any other suitable temperature sensor. The sensor probe 8 is connected to the rest of the gas sensing apparatus 2 with a cable or via wireless communications.

FIG. 3 shows a diagram of an embodiment in which the gas sensor 4 is an interstitial oxygen sensor 50. In this case the gas sensor 4 comprises a sensor probe 8 and an outer part 54. The sensor probe 8 punctures the skin 52 and measures oxygen concentrations in interstitial fluid. A retractable needle may be used to puncture the skin 52 and the gas sensor 4 transmits the measurements to the analysis system 30 and display device 35 wirelessly. Alternatively, the analysis system 30 may be disposed in the outer part 54, and the concentration determined by the analysis system 30 transmitted wirelessly to the display device 35. A temperature sensor 20 comprising a thermocouple or thermistor is provided to measure the skin temperature. This may be provided within the sensor probe 8 which penetrates the skin 52, or in proximity to the skin 52 within the outer part 54.

FIG. 4 shows a diagram of an embodiment in which the gas sensor 4 is a bypass sensor 60. Such sensors would be used in an external blood pump to monitor concentrations of gaseous substances in the blood being pumped. Similarly as described above for the case of a ventilator, measurements of blood gas concentration are used as part of the control of a blood pumping rate by the external blood pump, for example to maintain appropriate levels of oxygenation of blood. In this case, a disposable sensor probe 8 is mounted on a bypass loop 61 such that the sensing chemistry comprising the luminescent compound would contact the blood passing through it. A permanent, reusable optical/electrical connector 62 connects the disposable sensor probe 8 to the remainder of the gas sensing apparatus 2. A thermistor or another suitable temperature sensor 20 is mounted within the disposable sensor probe 8 to measure the temperature of the blood.

The gaseous substance to be detected may in general be any substance that is gaseous in isolation at a normal temperature and pressure (NTP), for example 288.15 K (15.00° C.) and 101.325 kPa. When measured the gaseous substance may be dissolved in a liquid.

The gaseous substance to be detected is typically one which can be found in a human or animal body, for example a blood gas (oxygen or carbon dioxide), nitric oxide which is a common signalling molecule, carbon monoxide, or an anaesthetic gas (e.g. nitrous oxide, isoflurane, sevoflurane, desflurane). Preferably, the gaseous substance to be detected is a blood gas (oxygen, carbon dioxide or nitrogen), preferably oxygen or carbon dioxide, most preferably oxygen.

The luminescent compound is a compound which is sensitive to the gaseous substance to be detected, such that it has a luminescence lifetime that is quenched by the gaseous substance. Typically, the luminescent compound has a lifetime, when quenched, of 10 ns or more, preferably 100 ns or more, more preferably 1 us or more. Typically the luminescent compound comprises a fluorescent compound. The luminescent compound is typically biocompatible. In one aspect the luminescent compound is an organic dye.

Where the gaseous substance to be detected is oxygen, the luminescent compound is typically an oxygen-sensitive organic dye. For example, the luminescent compound may be a polycyclic aromatic compound or a complex of a transition metal with one or more aromatic ligands, in particular polycyclic aromatic ligands. The transition metal may be, for example, platinum (e.g. platinum (II)), ruthenium (e.g. ruthenium (II)), palladium (e.g. palladium (II)), osmium (e.g. osmium (II)), iridium (e.g. iridium (III)), cobalt (e.g. cobalt (II)), or zinc. Platinum (e.g. platinum (II)), ruthenium (e.g. ruthenium (II)) and palladium (e.g. palladium (II)) are preferred. Most preferably, the luminescent compound is a platinum complex (e.g. a platinum (II) complex), most preferably a complex of platinum (II) with one or more aromatic ligands, in particular polycyclic aromatic ligands.

The polycyclic aromatic ligand(s) or polycyclic aromatic compound contains two or more aromatic rings which may be fused or non-fused. Examples include porphyrin, bipyridine, anthracene, floranthracene, phenanthrene, pyrene, perylene or decacyclene and derivatives thereof. Porphyrins and their derivatives are preferred. Examples of porphyrin derivatives that can be used either alone as the organic dye, or as a ligand in a transition metal complex, include phenyl porphyrins including tetraphenyl porphine (TPP, also known as tetraphenyl porphyrin) and halogenated versions of TPP including tetra (pentafluorophenyl)porphine (TFPP).

Most preferred luminescent compounds are therefore complexes of platinum (e.g. platinum (II)), ruthenium (e.g. ruthenium (II)) and palladium (e.g. palladium (II)), most preferably complexes of platinum (II), with porphyrin ligands, in particular complexes with tetraphenyl porphyrins and halogenated tetraphenyl porphyrins. A preferred luminescent compound is platinum (II) meso-tetra(pentafluorophenyl)porphine (PtTFPP).

Where the gaseous substance is other than oxygen, a luminescent compound should be chosen whose luminescence lifetime is quenched in the presence of the selected gaseous substance. Suitable luminescent compounds such as organic dyes, capable of being quenched in the presence of a blood gas, nitric oxide, carbon monoxide, or anaesthetic gas, are known in the art and could be selected by the skilled person.

The luminescent compound is preferably one which emits at wavelength different to excitation wavelength. Platinum (II) complexes are particularly suitable in this regard since their excitation and emission wavelengths are well separated. Platinum (II) complexes also provide relatively long luminescence lifetimes. The fluorescence of the platinum tetraphenyl porphyrin complexes is very efficiently quenched in the presence of oxygen.

The luminescent compound is suspended in, dissolved in, or molecularly bonded to, a matrix. Thus, the luminescent compounds may be physically entrapped within the matrix, or covalently bonded to the matrix. The matrix is permeable to the gaseous substance to be detected.

In one aspect, the matrix comprises a polymer. Polymeric matrices may be hydrophilic or hydrophobic. For example, the polymeric matrix may be a hydrogel, for example PHEMA or polyacrylamide. Acrylate polymers including PPMA, PMMA and PEMA may be used. Alternatively, the matrix may comprise a hydrophobic polymer, for example it may comprise polystyrene. Hydrophobic polymers are preferred because they protect the fluorophore from water soluble interferences, which is particularly relevant in blood gas sensing where water is prevalent in the environment.

In an alternative aspect, the matrix comprises a sol-gel. Sol-gel matrices for supporting luminescent compounds are described, for example, by Chu et al (Sensors and Actuators B 155 (2011) 53-57.

The reflector is formed of a material which is permeable to the gaseous substance to be detected and suitable for reflecting the light at the wavelength of the luminescence. Suitable materials include polymers such as polysulfones (PSU), polyethersulfones (PESU), polytetrafluroethylene (PTFE), polyethylene (PE), polypropylene (PP), and polyphenylsulfones (PPSU). Polysulfones are preferred. It would also be possible to use other reflecting compounds such as silicon containing titanium oxide, or barium sulfate. In some embodiments, the gaseous substance to be detected may be soluble in the material of the matrix. This can cause a lag in the response of the gas sensor to changes in the concentration of the gaseous substance in the environment. For example, if the concentration of the gaseous substance in the environment decreases rapidly, gas dissolved in the matrix may be released. The luminescent compound suspended in the matrix is exposed to the gas released by the matrix, and so experience a concentration of gaseous substance higher than that in the environment. Depending on the timescale over which the gas concentration in the matrix equilibrates with the gas concentration in the environment, the gas sensor may react only slowly to changes in the concentration of the gaseous substance in the environment.

It is therefore desirable to choose the material comprising the matrix such that the solubility of the gaseous substance does not cause too large a lag in the response time of the sensor. For example, it may be problematic if the response time of the sensor is much longer than the timescale over which the concentration of the gaseous substance typically changes in the environment. Polystyrene is an example of a suitable material for the matrix in the case where the sensor is configured to detect oxygen concentrations, because the solubility of oxygen in polystyrene is such as to not introduce a large time lag.

In the presence of a gaseous substance, the luminescence lifetime of a luminescent compound becomes quenched, i.e. reduced. Quenching of the luminescence lifetime is caused by collisions between excited molecules of the luminescent compound and molecules/particles of the gaseous substance. The collision between an excited molecule of luminescent compound and a molecule of gaseous substance causes the luminescent compound molecule to emit light immediately, thereby becoming unexcited. As the concentration of the gaseous substance increases, so too does the rate of such collisions, leading to a faster decay rate of the luminescence.

Prior to discussing a calibration method and gas sensing method, the model of the relationship between the luminescence lifetime and the concentration of the gaseous substance used as part of the methods will first be discussed.

For many luminescent compounds, the effect of quenching can be modelled used a Stern-Volmer equation, as shown in Eq. 1 for the case where the gaseous substance is oxygen. The Stern-Volmer equation has a linear relationship between $\tau_0/\tau$ and gaseous substance concentration:

$$\tau_0/\tau = 1 + K_{SV}[O_2] \quad \text{Eq. 1. Stern-Volmer Equation}$$

where:

$\tau$—fluorescence lifetime in presence of oxygen;
$\tau_0$—fluorescence lifetime in the absence of oxygen;
$K_{SV}$—Stern-Volmer constant (quantifies the quenching efficiency); and
$[O_2]$—oxygen concentration.

It is found that when the luminescent compound is incorporated into a sensor, the sensor functions by a quenching mechanism that does not follow a standard Stern-Volmer profile. In other words, the dependence of $\tau_0/\tau$ on the concentration of the gaseous substance is not linear, as shown in Eq. 1, but has a more complicated dependence (typically quadratic or even higher order) which varies from sensor to sensor.

The inventors have theorised that this effect is due to the fact that the luminescent compound (e.g. a platinum complex) used for the sensing of the gaseous substance (e.g. oxygen) may be immobilised in a matrix (e.g. comprising a polystyrene film) on the end of a fibre optic, which results in a proportion of the luminescent compound being unavailable for sensing the gaseous substance. This has led to the development of a model of the relationship between the luminescence lifetime and the concentration of the gaseous substance that is modified by a calibration factor representing a proportion of the luminescent compound not being exposed to the gaseous substance. However, the physical mechanism by which the incorporation into a sensor affects the dependence of luminescence lifetime on gaseous substance concentration may be different. For example, it may be the case that different proportions of the luminescent compound experience a range of "effective" concentrations of gaseous substance between zero and the actual concentration in the environment. Nonetheless, the model described herein has been found to account sufficiently accurately for the observed behaviour of the luminescent compound, and the invention is not limited by whether or not the particular physical mechanism underlying the model is actually the direct cause of the observed effect.

According to the model, the observed fluorescent lifetime is described by Eq. 2:

$$\tau_{obs} = \left(\frac{100-X}{100}\right)\tau_{real} + \left(\frac{X}{100}\right)\tau_0, \quad \text{Eq. 2}$$

where:

$\tau_{obs}$—observed fluorescence lifetime in presence of gaseous substance (e.g. oxygen);
$\tau_{real}$—fluorescence lifetime expected for isolated luminescent compound in presence of gaseous substance (e.g. oxygen); and
X—calibration factor (percentage of luminescent compound not exposed to gaseous substance).

When it is appropriate, depending on the luminescent compound being used, the model of the relationship between the luminescence lifetime and the concentration of the gaseous substance is in accordance with a Stern-Volmer equation. In such an embodiment, $\Sigma_{real}$ can be determined in accordance with a normal Stern-Volmer dependence on concentration.

Eq. 2 can be substituted into Eq. 1 to yield a modified Stern-Volmer equation, Eq. 3:

Eq. 3. Modified Stern-Volmer Equation $$\frac{\tau_0}{\left(\frac{\tau_{obs} - \left(\frac{X}{100}\right)\tau_0}{\left(\frac{100-X}{100}\right)}\right)} = 1 + K_{SV}[O_2],$$

which can be rearranged to Eq. 4

Eq. 4. Modified Stern-Volmer Equation $$\left(\frac{\tau_0 * (100-X)}{100\tau_{obs} - X\tau_0}\right) - 1 = K_{SV}[O_2].$$

The calibration factor X can then be determined using Eq. 5, derived from rearranging Eq. 4.

$$X = \frac{100\left(\tau_{obs} - \frac{\tau_0}{1+K_{SV}[O_2]}\right)}{\tau_0 - \frac{\tau_0}{1+K_{SV}[O_2]}} \quad \text{Eq. 5}$$

To more accurately determine the concentration of the gaseous substance in the environment, it is preferable to account for the temperature of the luminescent compound. In such a case, the model of the relationship between the luminescence lifetime and the concentration of the gaseous substance is dependent on temperature. This is advantageous because the luminescence lifetime of the luminescent compound may be temperature-dependent, so accounting for this improves the accuracy of the model.

Where the model of the relationship between the luminescence lifetime and the concentration of the gaseous substance is in accordance with a Stern-Volmer equation, the Stern-Volmer equation may include a Stern-Volmer constant that is dependent on temperature.

In addition, where the model of the relationship between the luminescence lifetime and the concentration of the gaseous substance is in accordance with a Stern-Volmer equation, the Stern-Volmer equation may include a value of the luminescence lifetime in the absence of quenching by the gaseous substance that is dependent on temperature.

This is advantageous because To and $K_{SV}$ may both be temperature sensitive. In particular, the Stern-Volmer constant may be linearly dependent on temperature. The value of the luminescence lifetime in the absence of quenching To may also be linearly dependent on temperature. An example of their temperature dependences is shown in Eq. 6 and Eq. 7:

$$K_{SV} = K_{SV,37°C} + (T-37)\cdot\beta \quad \text{Eq. 6}$$

where:

$K_{SV,37°C}$—Stern-Volmer constant at 37° C.
$\beta$—Gradient of $K_{SV}$ vs. temperature $$\tau_0 = \tau_{0,37°C}(T-37)\cdot\alpha \quad \text{Eq. 7}$$

where:

$\tau_{0,37°C}$—fluorescence lifetime in the absence of oxygen at 37° C.

α—Gradient of $\tau_0$ vs. temperature

Substituting Eq. 6 and Eq. 7 into Eq. 4 leads to a temperature-dependent Stern-Volmer equation.

$$\left(\frac{(\tau_{0.37°\,C.} + (T-37)\cdot\alpha)\cdot(100-X)}{100\tau_{obs} - X\cdot(\tau_{0.37°\,C.} + (T-37)\cdot\alpha)}\right) - 1 = \qquad \text{Eq. 8}$$

$$K_{SV\,37°\,C.} + (T-37)\cdot\beta\cdot[O_2]$$

Having discussed the model used in the gas sensing method and calibration method, we can now proceed to discuss the methods themselves.

Figure 6:
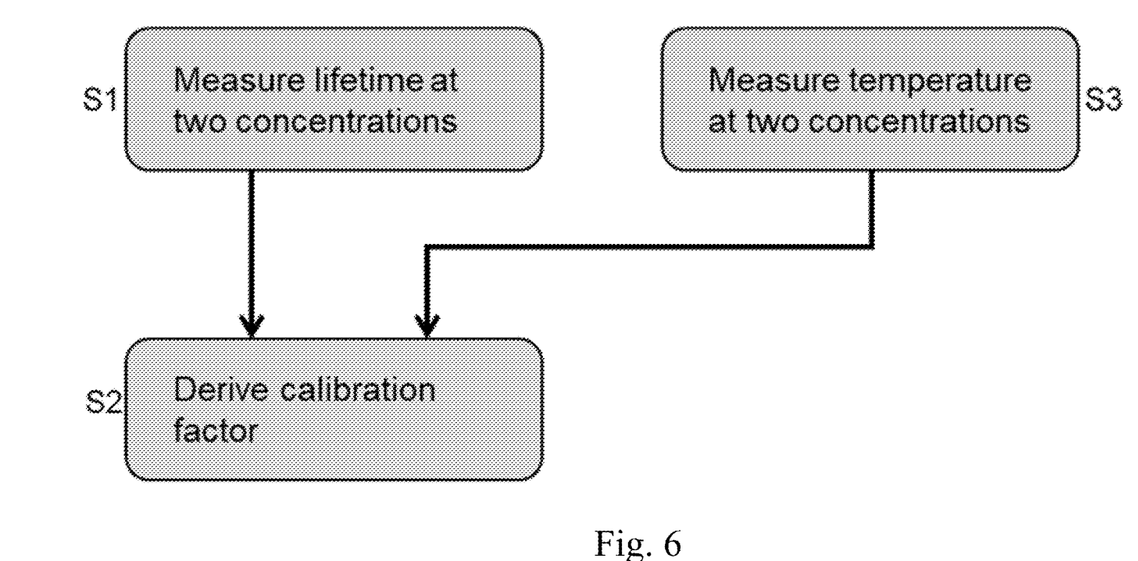
FIG. 6 shows a flowchart of a calibration method according to an embodiment.

FIG. 6 shows a flowchart for a calibration method of calibrating a gas sensor 4 comprising a luminescent compound having a luminescence lifetime that is quenched by a gaseous substance. The calibration method makes use of the model described above to simplify the procedure for calibrating the gas sensor 4, so that the demands on the end user are reduced. In particular, it makes it possible to calibrate the gas sensor 4 using only two known gas concentrations, which greatly reduces the time and complexity of equipment needed by the end user to calibrate the gas sensor 4.

The calibration method comprises the following steps.

In step S1, values of the luminescence lifetime of the luminescent compound are measured while the gas sensor 4 is exposed to at least two known concentrations of the gaseous substance. It does not matter in which order the known concentrations are measured. For example, the gas sensor 4 could initially be exposed to a higher concentration of gaseous substance, and subsequently a lower concentration, or vice versa.

In one example, said gaseous substance is present in air and one of said known concentrations of the gaseous substance is the concentration in air. This may be advantageous in the case where the gas sensor 4 is configured to detect a gaseous substance (e.g. oxygen or nitrogen) that has a reasonably consistent, known concentration in air, as it eliminates the need for specialised equipment to generate one of the known concentrations of gaseous substance.

When the gaseous substance is present in air, the gas sensor 4 may initially be packaged in an environment comprising a known concentration of the gaseous substance, and step S1 comprises measuring a first value of the luminescence lifetime while the gas sensor 4 is packaged in the known concentration of gaseous substance, and subsequently measuring a second value of the luminescence lifetime after opening the packaging and exposing the gas sensor 4 to air. Where the gas sensor 4 comprises a sensor probe 8, only the sensor probe 8 may be initially packaged in a known concentration of the gaseous substance.

This is particularly convenient in embodiments where the sensor probe 8 or gas sensor 4 are disposable and/or sterile. This is because the gas sensor 4 can be stored in the packaging until needed, calibrated immediately before use, and then disposed of after use. It also eliminates the need for any specialised equipment to generate the two known concentrations of gaseous substance.

Optionally, one of said known concentrations of the gaseous substance is a concentration of zero. This may be the case where the other of the known concentrations of the gaseous substance is the concentration in air, or alternatively, the other of the known concentrations may be provided otherwise. This embodiment is convenient because using a concentration of zero also allows the direct determination of $\tau_0$ as shown in the equations above, rather than having to extrapolate this from the measurements. This reduces the computational complexity of the calibration procedure. When the gas sensor 4 is packaged in an environment comprising a known concentration of the gaseous substance, it is particularly easy to package the gas sensor 4 such that the known concentration is zero. For example, the packaging may be evacuated, or the packaging may be filled with a gaseous substance other than the gaseous substance to be detected by the gas sensor 4. Additionally, a measurement of the luminescence lifetime can be made before unpacking the gas sensor 4, so the end user does not require any specialised equipment to generate a zero concentration of the gaseous substance for calibration.

In the case where the gas sensor apparatus 2 is used to measure blood gas concentrations, another option for one of the known concentrations of the gaseous substance would be to allow the gas sensor 4 to reach equilibrium with the concentration of the gaseous substance in the blood, and then take a blood sample. The concentration of gaseous substance in the blood sample can be determined using another technique, for example using a conventional blood-gas analyser, and the measurement of the luminescence lifetime taken at the same time as the blood sample would be at a known concentration obtained from analysing the blood sample.

It does not matter which order the measurements of luminescence lifetime in the two or more known concentrations are made. While in some embodiments, it is more convenient to measure the luminescence lifetime in the zero concentration first, this is not necessary for the calibration method to perform adequately.

Measuring a value of the luminescence lifetime may comprise: exciting the luminescent compound using a light source 10; measuring the intensity of light luminesced by the luminescent compound; and deriving the value of the luminescence lifetime from the measured intensity. The light source 10 may be a continuous light source with oscillating intensity, or a pulsed light source. Depending on the choice of light source 10, deriving the value of the luminescence lifetime is performed using the phase difference between the oscillations in the light used to excite the luminescent compound, and the oscillations in the light emitted by the luminescent compound, or by measuring the change in intensity during the time after the end of a pulse.

In step S2, the calibration factor is derived from the measured values of the luminescence lifetime using the model of the relationship between the luminescence lifetime and the concentration of the gaseous substance that is modified by a calibration factor representing a proportion of the compound not being exposed to the gaseous substance.

This allows a two-point measurement for easy calibration. For example, when the gas sensor apparatus 2 is configured to detect oxygen, a 2-point calibration can be carried out such that the initial calibration point is at 0% oxygen (using a modified atmosphere packaging for the gas sensor 4), and the second measurement at a higher oxygen concentration is made in air (which is approximately 20% oxygen).

As seen in Eq. 5 above, where the model is in accordance with a Stern-Volmer equation, the calibration factor is given by an equation including three constants $\tau_{obs}$, $\tau_0$, and $K_{SV}$. $K_{SV}$ is the quenching rate of the luminescent compound (e.g. a platinum complex) and therefore should be consistent sensor to sensor. Therefore it can be determined at the time of manufacturing. This means the two measurements made by the end user are sufficient to determine the calibration factor and calibrate the gas sensor 4.

In an embodiment where the gas sensor 4 further comprises a temperature sensor 20, the calibration method comprises a step S3 of measuring a temperature of the luminescent compound, and step S2 of deriving the calibration factor takes account of the temperature of the gas sensor 4 measured by the temperature sensor 20, the model of the relationship between the luminescence lifetime and the concentration of the gaseous substance being dependent on temperature. In such an embodiment, the model is as described above, i.e. the model may be in accordance with a Stern-Volmer equation and the Stern-Volmer constant and/or the luminescence lifetime in the absence of quenching by the gaseous substance may be dependent on temperature. Further, the temperature dependence of the Stern-Volmer constant and/or the temperature dependence of the luminescence lifetime in the absence of quenching by the gaseous substance ($\tau_0$) may be linear.

Where the temperature dependence of the Stern-Volmer constant and/or $\tau_0$ are linear, it may be the case that the constants $\alpha$ and $\beta$ are small and using an estimate for these values gives reasonable sensor accuracy. Therefore values for these constants determined at the time of manufacture can be used by the end user. This means that there are 3 remaining calibration constants that would need to be calculated prior to sensor use. They are $\tau_0$, $K_{SV}$, and X. Assuming $K_{SV}$ is a constant (as above) we can rearrange Eq. 2 to calculate X using the data collected as in Eq. 9.

$$X = \frac{100(\tau_{obs} - \tau_{real})}{\tau_0 - \tau_{real}} \quad \text{Eq. 9}$$

Substituting Eq. 1 into Eq. 9 gives Eq. 5 as discussed above. In an embodiment in which the gaseous substance is oxygen, this gives Eq. 10:

$$X = \frac{100\left(\tau_{obs} - \frac{\tau_{0 \cdot T_2}}{1 + K_{SV \cdot T_2}[O_2]}\right)}{\tau_{0 \cdot T_2} - \frac{\tau_{0 \cdot T_2}}{1 + K_{SV \cdot T_2}[O_2]}} \quad \text{Eq. 10}$$

Figure 5:
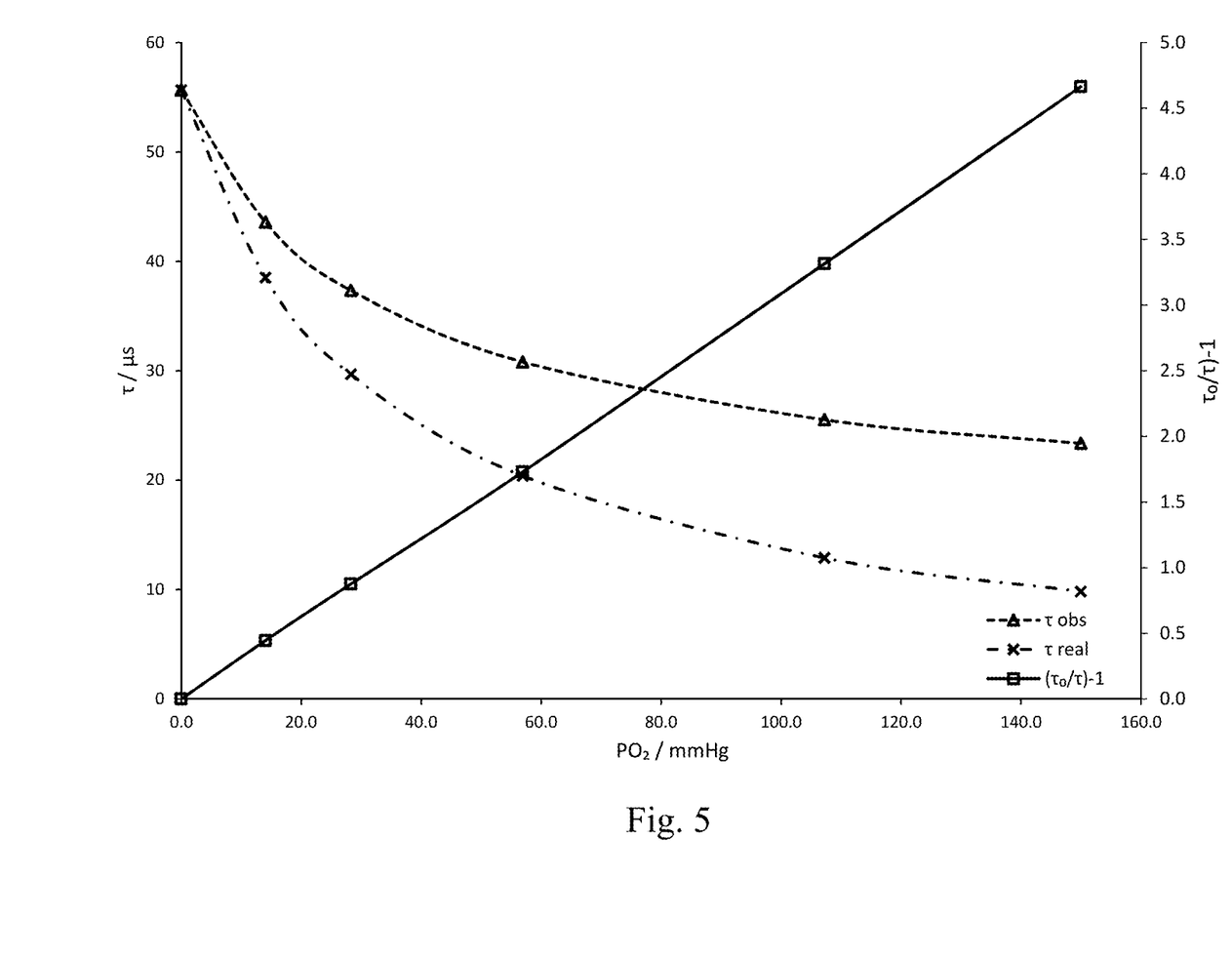
FIG. 5 shows an example of measurements of fluorescence lifetime as a function of oxygen concentration.

Substituting Eq. 6 and Eq. 7 into Eq. 10 gives Eq. 11, $$X = \frac{100\left(\tau_{obs} - \frac{\tau_{0 \cdot Obs} + (T_2 - T_1)\alpha}{1 + (K_{SV\ 37^\circ\ C.} + (T_2 - 37) \cdot \beta)[O_2]}\right)}{(\tau_{0 \cdot Obs} + (T_2 - T_1)\alpha) - \frac{\tau_{0 \cdot Obs} + (T_2 - T_1)\alpha}{1 + (K_{SV\ 37^\circ\ C.} + (T_2 - 37) \cdot \beta)[O_2]}} \quad \text{Eq. 11}$$

which can be rearranged to give Eq. 12.

$$X = \frac{100((\tau_{obs} + (K_{SV\ 37^\circ\ C.} + (T_2 - 37) \cdot \beta)[O_2]\tau_{obs} - (\tau_{0 \cdot Obs} + (T_2 - T_1)\alpha))}{((K_{SV\ 37^\circ\ C.} + (T_2 - 37) \cdot \beta)[O_2])(\tau_{0 \cdot Obs} + (T_2 - T_1)\alpha)} \quad \text{Eq. 12}$$

where:
$\tau_{Obs}$—Measured lifetime at $T^2$
$\tau_{0.Obs}$—Measured $\tau_0$ at
$\tau_{0.\ T2}$—Calculated $\tau_0$ at $T_2$
$\alpha$—Gradient of $\tau_0$ vs. temperature
$K_{SV\ 37^\circ\ C.}$—Stern-Volmer constant at 37° C.
$K_{SV.T2}$ Stern-Volmer constant at $T_2$
$\beta$—Gradient of $K_{SV}$ vs. temperature
$T_1$—Temperature at first calibration point (0% oxygen)
$T_2$—Temperature at second calibration point (oxygen present)
$[O_2]$—Oxygen concentration at second calibration point Effectively, the use of Eq. 11 or 12 to determine the calibration factor allows a linear relationship between $\tau_o/\tau$ and gaseous substance concentration to be used in respect of the portion of the luminescent compound that is exposed to the gaseous substance, simplifying the calculation and necessitating only two calibration measurements to derive the linear relationship. This is illustrated in FIG. 5, which shows how in an example embodiment, the dependence of $\tau_o/\tau$ on oxygen concentration is linear once the luminescence lifetime is corrected to account for the proportion of the luminescent compound not exposed to oxygen.

Specifically, FIG. 5 shows the calibration of a gas sensor 4 against six different oxygen concentrations. Once $\tau_{REAL}$ is calculated the resulting Stern-Volmer plot is linear as expected. In this case 29.5% of the fluorescent dye is unavailable for sensing. For the measurements in FIG. 5, $\tau_o$=55.7 µs, $K_{SV}$=0.031, X=29.5%.

In the calibration method, the gaseous substance and the luminescent compound may be any of the substances or classes of substances as described above. The gas sensor 4 used in the calibration method is constructed as described above.

Having described the calibration method, we now move on to discussing the gas sensing method.

Figure 7:
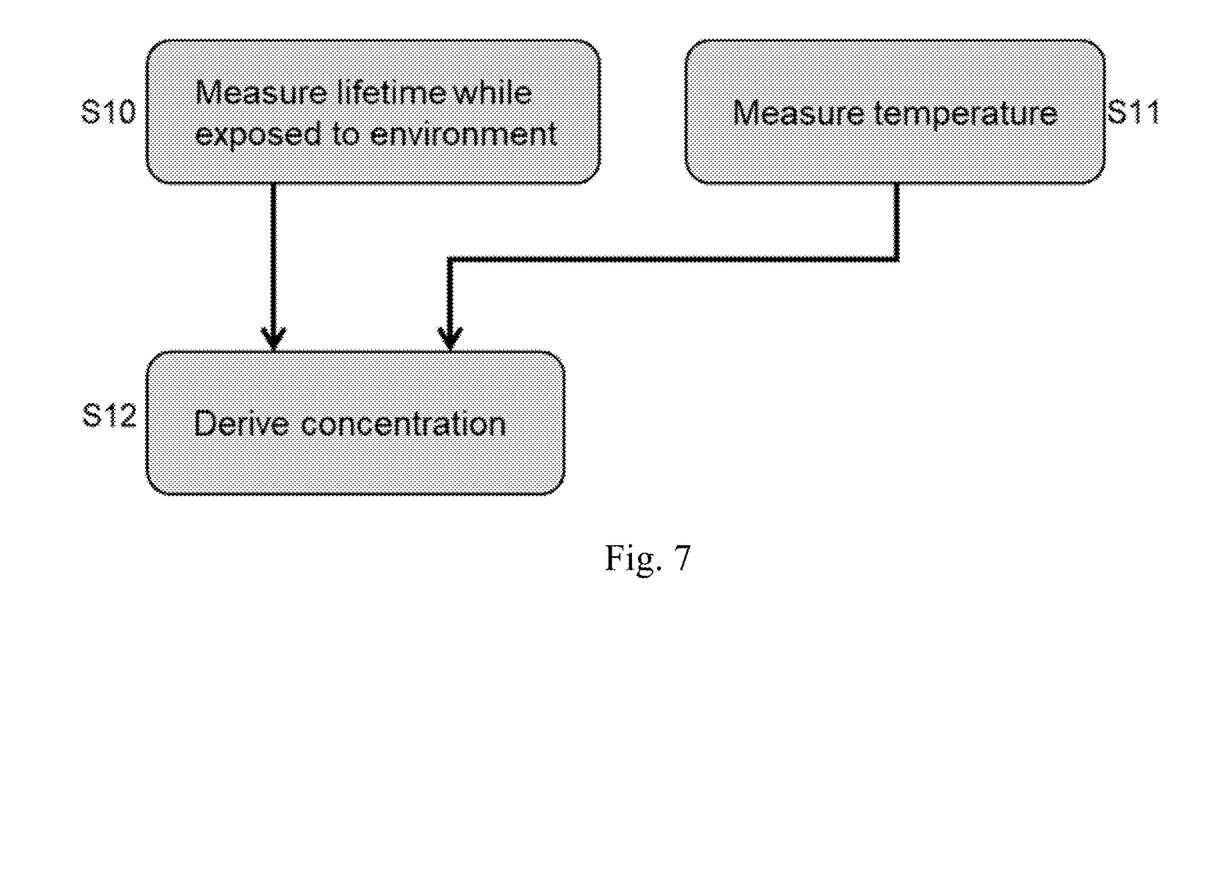
FIG. 7 shows a flowchart of a gas sensing method according to an embodiment.

FIG. 7 shows a flowchart of a gas sensing method of measuring a concentration of a gaseous substance in an environment using a gas sensor, the gas sensor comprising a luminescent compound having a luminescence lifetime that is quenched by the gaseous substance. The gas sensing method makes use of the model described above to provide a gas sensing method corresponding to the calibration method, which is simple and convenient for the end user.

The gas sensing method comprises the following steps.

In step S10, a value of the luminescence lifetime of the luminescent compound is measured while the gas sensor is exposed to the environment. The environment may be inside of a human or animal body. For example, the environment may be inside a blood vessel or the interior of body tissue. In such embodiments, the gas sensing method may be used to measure the concentration of gases dissolved in blood or interstitial fluid. Alternatively, the environment may be another liquid environment in which it is desirable to measure the concentration of dissolved gaseous substances. For example, the gas sensing method may be used to measure the concentration of blood gases in a blood loop, where the blood is circulated external to the human or animal body by means of a blood pump. In this case, the environment is the interior of the blood-carrying parts of the blood pump. Although these examples represent preferred uses for the gas sensing method, the gas sensing method is not limited to measuring the concentration of gaseous substances dissolved in liquids, and is also suitable for use in measuring the concentration of gaseous substances in free, gaseous form.

Measuring a value of the luminescence lifetime may comprise: exciting the luminescent compound using a light source 10; measuring the intensity of light luminesced by the luminescent compound; and deriving the value of the luminescence lifetime from the measured intensity. The light source 10 may be a continuous light source with oscillating intensity, or a pulsed light source. Depending on the choice of light source 10, deriving the value of the luminescence lifetime is performed using the phase difference between the oscillations in the light used to excite the luminescent compound, and the oscillations in the light emitted by the luminescent compound, or by measuring the change in intensity during the time after the end of a pulse.

In step S12 a concentration of the gaseous substance is derived from the measured luminescence lifetime using a model of the relationship between the luminescence lifetime and the concentration of the gaseous substance that is modified by a calibration factor representing a proportion of the luminescent compound not being exposed to the gaseous substance.

In an embodiment where the gas sensor 4 further comprises a temperature sensor 20, the gas sensing method further comprises a step S11 of measuring a temperature of the gas sensor 4, and the step S12 of deriving a concentration of the gaseous substance takes account of the temperature of the gas sensor 4 measured by the temperature sensor 20, the model of the relationship between the luminescence lifetime and the concentration of the gaseous substance being dependent on temperature. In such an embodiment, the model is as described above, i.e. the model may be in accordance with a Stern-Volmer equation and the Stern-Volmer constant and/or the luminescence lifetime in the absence of quenching by the gaseous substance may be dependent on temperature. Further, the temperature dependence of the Stern-Volmer constant and/or the temperature dependence of the luminescence lifetime in the absence of quenching by the gaseous substance ($\tau_0$) may be linear.

The step of deriving a concentration of the gaseous substance from the measured lifetime may comprise deriving a luminescence lifetime of the proportion of the luminescent compound exposed to the gaseous substance ($\tau_{real}$) and deriving a concentration of the gaseous substance from the luminescence lifetime of the proportion of the luminescent compound exposed to the gaseous substance. The deriving of a concentration of the gaseous substance from the luminescence lifetime of the proportion of the luminescent compound exposed to the gaseous substance may involve using a Stern-Volmer relationship for the dependence of the luminescence lifetime of the proportion of the luminescent compound exposed to the gaseous substance on the concentration of the gaseous substance.

In the gas sensing method, the gaseous substance and the luminescent compound may be any of the substances or classes of substances as described above. The gas sensor 4 used in the gas sensing method is constructed as described above.

There will now be described the results of experiments to verify the accuracy of the concentrations of gaseous substance determined using embodiments of the invention. The experiments were carried out using an embodiment in which the gaseous substance was oxygen, the matrix was polystyrene, and the luminescent compound was a fluorescent organic dye (platinum (II) meso-tetra(pentafluorophenyl) porphine (PtTFPP).

Using Eq. 11 two sensors were calibrated at 0 and 150 mmHg at 30° C. Table 1 shows the calibration constants used to calculate X.

TABLE 1

Calibration constants used to calculate X.

| Calibration Constant | Predicted Values |
|---|---|
| $K_{SV,37°C.}$ | 0.0257 |
| α | −0.240 |
| β | 0.0002 |

For sensor 007-011, X=28.31, for sensor 007-002, X=34.08. Table 2 shows the accuracy testing for the two sensors. The testing measured oxygen concentrations between 0 and 290 mmHg at 30, 37, and 40° C. and resulted in mean absolute relative differences (MARDs) of 5.3 and 5.5% for the individual sensors. The accuracy data from this testing is shown in Table 2.

TABLE 2

Accuracy data for 2 sensors, labelled sensor 007-011 and sensor 007-002.

| pO$_2$/mmHg | | | +/−/mmHg | | +/− % | | Absolute Errors | |
|---|---|---|---|---|---|---|---|---|
| Reference | 007-011 | 007-002 | 007-011 | 007-002 | 007-011 | 007-002 | 007-011 | 007-002 |
| 0.00 | 0.00 | 0.00 | 0.00 | 0.00 | | | | |
| 14.10 | 16.66 | 15.92 | 2.56 | 1.81 | 18.13 | 12.86 | 18.13 | 12.86 |
| 28.57 | 31.97 | 29.62 | 3.40 | 1.05 | 11.92 | 3.69 | 11.92 | 3.69 |
| 57.63 | 61.44 | 57.26 | 3.81 | −0.37 | 6.61 | −0.64 | 6.61 | 0.64 |
| 108.42 | 110.01 | 104.45 | 1.59 | −3.98 | 1.47 | −3.67 | 1.47 | 3.67 |
| 150.78 | 150.78 | 150.78 | 0.00 | 0.00 | 0.00 | 0.00 | 0.00 | 0.00 |
| 288.61 | 289.37 | 322.93 | 0.76 | 34.32 | 0.26 | 11.89 | 0.26 | 11.89 |
| 0.00 | −0.07 | 0.06 | −0.07 | 0.06 | | | | |
| 13.87 | 16.57 | 15.87 | 2.70 | 2.00 | 19.45 | 14.41 | 19.45 | 14.41 |
| 28.11 | 31.25 | 29.60 | 3.14 | 1.50 | 11.19 | 5.33 | 11.19 | 5.33 |
| 56.71 | 59.68 | 56.89 | 2.97 | 0.18 | 5.24 | 0.31 | 5.24 | 0.31 |
| 106.77 | 106.83 | 106.98 | 0.06 | 0.20 | 0.06 | 0.19 | 0.06 | 0.19 |
| 148.44 | 147.71 | 150.62 | −0.73 | 2.18 | −0.49 | 1.47 | 0.49 | 1.47 |
| 284.24 | 283.52 | 325.31 | −0.71 | 41.07 | −0.25 | 14.45 | 0.25 | 14.45 |
| 0.00 | −0.95 | −0.25 | −0.95 | −0.25 | | | | |
| 13.66 | 15.42 | 15.16 | 1.76 | 1.50 | 12.90 | 11.00 | 12.90 | 11.00 |
| 27.69 | 30.10 | 29.73 | 2.41 | 2.03 | 8.69 | 7.35 | 8.69 | 7.35 |
| 55.86 | 57.72 | 56.63 | 1.85 | 0.77 | 3.32 | 1.38 | 3.32 | 1.38 |
| 105.15 | 104.11 | 105.24 | −1.04 | 0.09 | −0.99 | 0.09 | 0.99 | 0.09 |
| 146.15 | 142.14 | 149.18 | −4.01 | 3.03 | −2.74 | 2.07 | 2.74 | 2.07 |
| 280.43 | 278.22 | 320.50 | −2.21 | 40.07 | −0.79 | 14.29 | 0.79 | 14.29 |
| | | | 0.40 | 6.08 | 4.47 | 5.10 | 5.33 | 5.54 |

The invention claimed is:

1. A method of measuring a concentration of a gaseous substance in an environment using a gas sensor comprising a luminescent compound having a luminescence lifetime that is quenched by the gaseous substance and a temperature sensor configured to measure a temperature of the luminescent compound, the method comprising:
   measuring a value of the luminescence lifetime of the luminescent compound while the gas sensor is exposed to the environment; and
   deriving a concentration of the gaseous substance from the measured luminescence lifetime taking account of the temperature of the luminescent compound measured by the temperature sensor, the derivation using a model of the relationship between the luminescence lifetime and the concentration of the gaseous substance that is in accordance with a Stern-Volmer equation and that is modified by a calibration factor representing a proportion of the luminescent compound not being exposed to the gaseous substance, the Stern-Volmer equation including a Stern-Volmer constant that is dependent on temperature, and/or a value of the luminescence lifetime in the absence of quenching by the gaseous substance that is dependent on temperature.

2. A method according to claim 1, wherein the Stern-Volmer constant is linearly dependent on temperature.

3. A method according to claim 1, wherein the value of the luminescence lifetime in the absence of quenching is linearly dependent on temperature.

4. A method according to claim 1, wherein measuring a value of the luminescence lifetime comprises:

exciting the luminescent compound using a light source;
measuring the intensity of light luminesced by the luminescent compound; and
deriving the value of the luminescence lifetime from the measured intensity.

5. A method according to claim 1, wherein the gaseous substance comprises oxygen.

6. A method according to claim 1, wherein the luminescent compound comprises a platinum complex.

7. A method according to claim 1, wherein the luminescent compound is suspended in, dissolved in, or molecularly bonded to, a matrix comprising a polymer or a sol-gel.

8. A method according to claim 7, wherein the matrix comprises polystyrene.

9. A method according to claim 1, wherein the environment is inside of a human or animal body.

10. A method of calibrating a gas sensor comprising a luminescent compound having a luminescence lifetime that is quenched by a gaseous substance and a temperature sensor configured to measure a temperature of the luminescent compound, the method using a model of the relationship between the luminescence lifetime and the concentration of the gaseous substance that is modified by a calibration factor representing a proportion of the compound not being exposed to the gaseous substance, the method comprising:
measuring values of the luminescence lifetime of the luminescent compound while the gas sensor is exposed to at least two known concentrations of the gaseous substance; and
deriving the calibration factor from the measured values of the luminescence lifetime using the model taking account of the temperature of the luminescent compound measured by the temperature sensor,
wherein the model of the relationship between the luminescence lifetime and the concentration of the gaseous substance is in accordance with a Stern-Volmer equation, the Stern-Volmer equation including a Stern-Volmer constant that is dependent on temperature and/or a value of the luminescence lifetime in the absence of quenching by the gaseous substance that is dependent on temperature.

11. A method according to claim 10, wherein one of said known concentrations of the gaseous substance is a concentration of zero.

12. A method according to claim 10, wherein said gaseous substance is present in air and one of said known concentrations of the gaseous substance is the concentration in air.

13. A method according to claim 10, wherein the Stern-Volmer constant is linearly dependent on temperature.

14. A method according to claim 10, wherein the value of the luminescence lifetime in the absence of quenching is linearly dependent on temperature.

15. A method according to claim 10, wherein measuring a value of the luminescence lifetime comprises:
exciting the luminescent compound using a light source;
measuring the intensity of light luminesced by the luminescent compound; and
deriving the value of the luminescence lifetime from the measured intensity.

16. A method according to claim 10, wherein the gaseous substance comprises oxygen.

17. A method according to claim 10, wherein the luminescent compound comprises a platinum complex.

18. A method according to claim 10, wherein the luminescent compound is suspended in, dissolved in, or molecularly bonded to, a matrix comprising a polymer or a sol-gel.

19. A method according to claim 18, wherein the matrix comprises polystyrene.

20. A gas sensor apparatus for measuring the concentration of a gaseous substance in an environment, the gas sensor apparatus comprising:
a gas sensor comprising a luminescent compound having a luminescence lifetime that is quenched by the gaseous substance, a temperature sensor configured to measure a temperature of the luminescent compound, and a detector configured to detect light emitted by the luminescent compound; and
an analysis system configured to derive a luminescence lifetime of the compound from the signal output by the detector, and to derive a concentration of the gaseous substance from the measured luminescence lifetime taking account of the temperature of the luminescent compound measured by the temperature sensor, the derivation using a model of the relationship between the luminescence lifetime and the concentration of the gaseous substance that is in accordance with a Stern-Volmer equation and that is modified by a calibration factor representing a proportion of the luminescent compound not being exposed to the gaseous substance, the Stern-Volmer equation including a Stern-Volmer constant that is dependent on temperature, and/or a value of the luminescence lifetime in the absence of quenching by the gaseous substance that is dependent on temperature.

21. A gas sensor apparatus according to claim 20, wherein the Stern-Volmer constant is linearly dependent on temperature.

22. A gas sensor apparatus according to claim 20, wherein the value of the luminescence lifetime in the absence of quenching is linearly dependent on temperature.

23. A gas sensor apparatus according to claim 20, wherein the gas sensor further comprises a light source configured to excite the luminescent compound.

24. A gas sensor apparatus according to claim 20, wherein the signal output by the detector represents the intensity of light luminesced by the luminescent compound.

25. A gas sensor apparatus according to claim 20, wherein the gas sensor comprises an optical fibre, the luminescent compound is arranged at an end of the optical fibre, and the optical fibre is arranged to guide light from the luminescent compound to the detector.

26. A gas sensor apparatus according to claim 25, wherein the apparatus further comprises a reflector extending around the luminescent compound and configured to reflect light luminesced by the luminescent compound into the optical fibre.

27. A gas sensor apparatus according to claim 26, wherein the reflector is permeable to the gaseous substance.

28. A gas sensor apparatus according to claim 20, wherein the gaseous substance comprises oxygen.

29. A gas sensor apparatus according to claim 20, wherein the luminescent compound comprises a platinum complex.

30. A gas sensor apparatus according to claim 20, wherein the gas sensor comprises a matrix comprising a polymer or a sol-gel, and the luminescent compound is suspended in, dissolved in, or molecularly bonded to, the matrix.

31. A gas sensor apparatus according to claim 30, wherein the matrix comprises polystyrene.

* * * * *